US00PP15882P2

(12) United States Plant Patent
Kobayashi

(10) Patent No.: US PP15,882 P2
(45) Date of Patent: Jul. 19, 2005

(54) *POINSETTIA* PLANT NAMED 'PER1055'

(50) Latin Name: *Euphorbia pulcherrima*
Varietal Denomination: PER1055

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/955,480

(22) Filed: Sep. 30, 2004

(51) Int. Cl.[7] ..... A01H 5/00
(52) U.S. Cl. ..... Plt./307
(58) Field of Search ..... Plt./307

(56) References Cited

U.S. PATENT DOCUMENTS

PP5,492 P * 6/1985 Gutbier ..... Plt./307
PP7,825 P * 3/1992 Fruehwirth ..... Plt./307
PP7,879 P * 6/1992 Fruehwirth ..... Plt./307
PP11,105 P * 10/1999 Dummen ..... Plt./307
PP11,872 P2 * 5/2001 Fruehwirth ..... Plt./307
PP12,719 P2 * 6/2002 Drewlow ..... Plt./307
PP13,297 P2 * 12/2002 Kobayashi ..... Plt./307
PP13,328 P2 * 12/2002 Kobayashi ..... Plt./307

OTHER PUBLICATIONS

UPOV ROM GTITM Computer Database, GTI Jouve Retrieval Software 2004/05 Citation for 'PER1055'.*

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Poinsettia* plant named 'PER1055', characterized by its inflorescences with bright red-colored flower bracts; dark green-colored leaves; uniform, compact, upright and mounded plant habit; early season flowering; natural season flower maturity date in late November for plants grown in Encinitas, Calif.; and excellent post-production longevity.

1 Drawing Sheet

Botanical designation: *Euphorbia pulcherrima* Willd.
Variety denomination: 'PER1055'.

BACKGROUND OF THE INVENTION

The present Invention relates to a new and distinct cultivar of *Poinsettia* plant, botanically known as *Euphorbia pulcherrima* Willd., and hereinafter referred to by the name 'PER1055'.

The new *Poinsettia* is a product of a planned breeding program conducted by the Inventor in Encinitas, Calif. The objective of the breeding program is to create new early flowering *Poinsettia* cultivars having strong stems, attractive flower bract coloration, uniform plant habit and excellent post-production longevity.

The new *Poinsettia* originated from an open-pollination made by the Inventor in December, 1999, of two unidentified selections of *Euphorbia pulcherrima* Willd. The cultivar PER1055 was discovered and selected by the Inventor as a single flowering plant within the progeny of the stated open-pollination in a controlled environment in Encinitas, Calif., in Dec., 2000.

Asexual reproduction of the new *Poinsettia* by terminal cuttings propagated in a controlled environment in Encinitas, Calif., since July, 2001, has shown that the unique features of this new *Poinsettia* are stable and reproduced true to type in successive generations of asexual reproduction.

BRIEF SUMMARY OF THE INVENTION

The following traits have been repeatedly observed and are determined to be the unique characteristics of 'PER1055'. These characteristics in combination distinguish 'PER1055' as a new and distinct cultivar:

1. Inflorescences with bright red-colored flower bracts.
2. Dark green-colored leaves.
3. Uniform, compact, upright and mounded plant habit.
4. Early season flowering; natural season flower maturity date is late November for plants grown in Encinitas, Calif.
5. Excellent post-production longevity.

Plants of the new *Poinsettia* can be compared to plants of the cultivar 490 (U.S. Plant Pat. No. 7,825). In side-by-side comparisons conducted in Encinitas, Calif., plants of the new *Poinsettia* differed primarily in time to flower as plants of the new *Poinsettia* flowered about one week later than plants of the cultivar 490. In addition, plants of the new *Poinsettia* had lighter-colored leaves and flower bracts than plants of the cultivar 490.

Plants of the new *Poinsettia* can also be compared to plants of the cultivar Angelika (U.S. Plant Pat. No. 5,492). In side-by-side comparisons conducted in Encinitas, Calif., plants of the new *Poinsettia* had brighter red-colored flower bracts than plants of the cultivar 490.

BRIEF DESCRIPTION OF THE PHOTOGRAPHS

The accompanying colored photographs illustrate the overall appearance of the new *Poinsettia,* showing the colors as true as it is reasonably possible to obtain in colored reproductions of this type. Colors in the photographs may differ slightly from the color values cited in the detailed botanical description which accurately describe the colors of the new *Poinsettia.*

The photograph at the top of the sheet comprises a side perspective view of a typical flowering plant of 'PER1055' grown in a container.

The photograph at the bottom left of the sheet is a close-up view of typical inflorescences of 'PER1055'.

The photograph at the bottom right of the sheet comprises a top perspective view of a typical plant of 'PER1055'.

DELAILED BOTANICAL DESCRIPTION

The new *Poinsettia* has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polyethylene-covered greenhouse with day temperatures averaging about 24° C., night temperatures averaging about 19° C. and light levels about 4,000 foot-candles. Single plants were grown in 16.5-cm pots and pinched once. Plants were flowered under natural season short day/long night conditions. Plants were about 15 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER1055.

Parentage:

*Female parent.*—Unknown selection of *Euphorbia pulcherrima* Willd.

*Male parent.*—Unknown selection of *Euphorbia pulcherrima* Willd.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous, freely-branching; white in color.

Plant description:

*Plant form.*—Inverted triangle; top of plant mounded.

*Growth habit.*—Upright, compact and uniform plant habit. Vigorous.

*Plant height.*—About 27 cm.

*Plant diameter or spread.*—About 34 cm.

*Lateral branch description.*—Quantity: About eight lateral branches develop after pinching. Length: About 22 cm. Diameter: About 5 mm. Internode length: About 2 cm. Strength: Strong. Texture: Smooth; glabrous. Color: 144A.

*Foliage description.*—Arrangement: Alternate, single. Length: About 15 cm. Width: About 9.5 cm. Shape: Elliptic. Apex: Acuminate. Base: Obtuse to slightly attenuate. Margin: Entire with irregular lobing. Venation pattern: Pinnate. Texture, upper and lower surfaces: Glabrous, smooth. Surface: Slightly rugose. Aspect: Mostly flat. Orientation: Mostly horizontal to slightly angled downward. Color: Developing foliage, upper surface: 146A. Developing foliage, lower surface: 147B. Fully expanded foliage, upper surface: Darker than 147A. Fully expanded foliage, lower surface: 147B. Venation, upper surface: 147B. Venation, lower surface: 147C. Petiole: Length: About 4.8 cm. Diameter: About 2.5 mm. Texture, upper and lower surfaces: Smooth; glabrous. Color: 185A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early season flowering, response time, about 8 weeks; natural season flower maturity date is late November for plants grown in Encinitas, Calif.

*Post-production longevity.*—Plants of the new *Poinsettia* maintain good substance and bract color for about four weeks under interior conditions.

*Inflorescence size.*—Diameter: About 28 cm. Height (depth): About 4 cm.

*Flower bracts.*—Quantity per inflorescence: About 16. Length, largest bracts: About 12.5 cm. Width, largest bracts: About 8.5 cm. Shape: Elliptic Apex: Acuminate. Base: Obtuse. Margin: Entire with irregular lobing, Texture, upper and lower surfaces: Glabrous; velvety. Surface: Initially, rugose, becoming mostly smooth with development. Aspect: Mostly flat. Orientation: Mostly horizontal to slightly downward with development. Venation pattern: Pinnate. Color: Developing or transitional bracts, upper surface: 53A. Developing or transitional bracts, lower surface: 53B. Fully developed bracts, upper surface: 46A; color does not fade with development. Fully developed bracts, lower surface: 47A. Venation, upper and lower surfaces: Similar to flower bract color. Bract petiole: Length: About 3.2 cm. Diameter: About 2 mm. Texture, upper and lower surfaces: Smooth; glabrous. Color: 46A.

*Cyathia.*—Quantity per corymb: About ten. Diameter of cyathia cluster: About 2.8 cm. Length: About 1 cm. Width: About 5 to 6 mm. Shape: Ovoid. Color, immature: 146B. Color, mature: 146A. Peduncle: Length: About 1.5 mm. Diameter: About 2 mm. Strength: Strong. Aspect: Mostly upright. Texture: Smooth; glabrous. Color: 146B. Stamens: Quantity per cyathium: About four to five. Anther shape: Bi-lobed. Anther length: About 1 mm. Anther color: 45C. Amount of pollen: Scarce. Pollen color: 12A. Pistils: None observed. Nectaries: Quantity per cyathium: About one or two. Size: About 4 mm by 6 mm. Color: 13A.

Disease/pest resistance: Resistance to pathogens and pests common to *Poinsettias* has not been observed on plants grown under commercial conditions.

It is claimed:

1. A new and distinct cultivar of *Poinsettia* plant named 'PER1055', as illustrated and described.

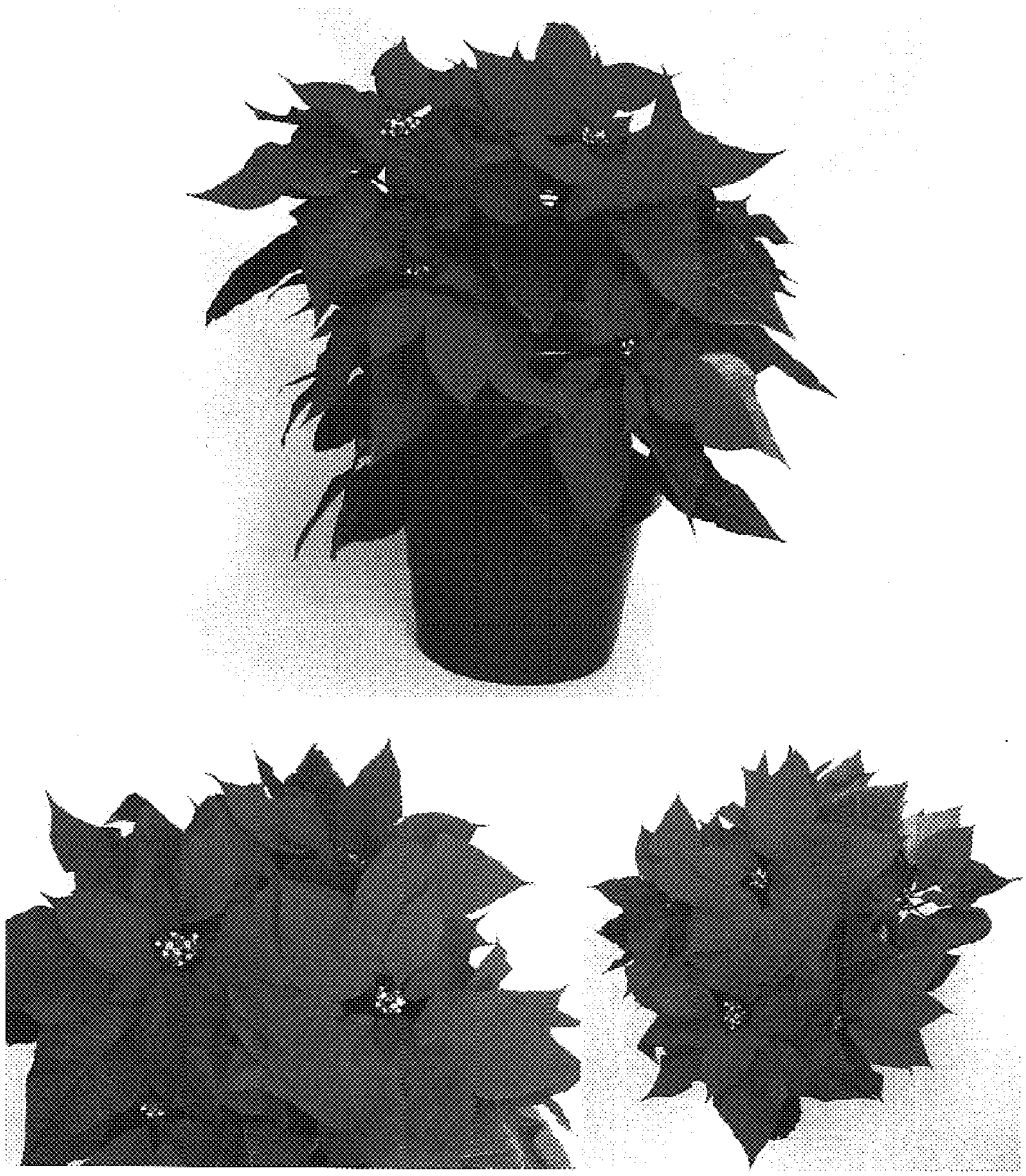

* * * * *